(12) United States Patent
Schweizer et al.

(10) Patent No.: US 9,592,408 B2
(45) Date of Patent: Mar. 14, 2017

(54) DOSE-VOLUME KERNEL GENERATION

(75) Inventors: Bernd Schweizer, Herzogenrath (DE); Andreas Goedicke, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 12/935,312

(22) PCT Filed: Mar. 20, 2009

(86) PCT No.: PCT/IB2009/051191
§ 371 (c)(1),
(2), (4) Date: Sep. 29, 2010

(87) PCT Pub. No.: WO2009/130622
PCT Pub. Date: Oct. 29, 2009

(65) Prior Publication Data
US 2011/0029329 A1   Feb. 3, 2011

Related U.S. Application Data

(60) Provisional application No. 61/047,443, filed on Apr. 24, 2008.

(51) Int. Cl.
| | | |
|---|---|---|
| *G01J 1/42* | (2006.01) | |
| *A61N 5/10* | (2006.01) | |
| *G06Q 50/24* | (2012.01) | |
| *G06F 19/00* | (2011.01) | |

(52) U.S. Cl.
CPC .......... *A61N 5/1031* (2013.01); *G06Q 50/24* (2013.01); *G06F 19/3437* (2013.01); *G06F 19/3481* (2013.01)

(58) Field of Classification Search
CPC ..... A61B 6/5288; A61B 5/7289; A61B 6/032; A61B 6/00; A61K 49/04; A61K 41/0028; A61K 41/0095; A61N 5/103; A61N 5/1049; A61N 2005/1098; A61N 5/10;
(Continued)

(56) References Cited

U.S. PATENT DOCUMENTS

| | | |
|---|---|---|
| 5,844,241 A | 12/1998 | Liu et al. |
| 6,148,272 A | 11/2000 | Bergstrom et al. |
| 6,301,329 B1 | 10/2001 | Surridge |

(Continued)

FOREIGN PATENT DOCUMENTS

WO   0040298 A1   7/2000

OTHER PUBLICATIONS

Erdi, A. K., et al.; Use of the fast Hartley transform for three-dimensional dose calculation in radionuclide therapy; 1998; Med. Phys.; 25(11)2226-2233.

(Continued)

*Primary Examiner* — Reginald R Reyes

(57) ABSTRACT

A radiation planning system includes a dose volume kernel determiner (122) and an expected absorbed dose determiner (124). The dose volume kernel determiner (122) generates a dose volume kernel for each of a plurality of voxels in a dose calculation grid. Each of the dose volume kernels is based on a radial dose distribution and a template function for a particular voxel size. The expected absorbed dose determiner (124) determines an expected absorbed dose distribution for each of the plurality of voxels based on the dose volume kernel.

28 Claims, 4 Drawing Sheets

(58) Field of Classification Search
CPC ......... G06T 7/0012; G06T 2207/10104; G06T 2207/10108
USPC .......................................................... 705/2
See application file for complete search history.

(56) References Cited

U.S. PATENT DOCUMENTS

| | | | | |
|---|---|---|---|---|
| 6,411,675 | B1* | 6/2002 | Llacer | 378/65 |
| 6,792,073 | B2 | 9/2004 | Deasy et al. | |
| 6,867,774 | B1 | 3/2005 | Halmshaw et al. | |
| 7,945,022 | B2* | 5/2011 | Nelms et al. | 378/65 |
| 2001/0037046 | A1* | 11/2001 | Weinberger et al. | 600/3 |
| 2003/0093419 | A1* | 5/2003 | Bangalore et al. | 707/3 |
| 2005/0041843 | A1* | 2/2005 | Sawyer | A61N 5/1049 382/128 |
| 2007/0275080 | A1* | 11/2007 | Laulicht et al. | 424/493 |
| 2008/0091388 | A1* | 4/2008 | Failla | A61N 5/1031 703/2 |
| 2008/0292153 | A1* | 11/2008 | Binnig et al. | 382/128 |
| 2008/0306770 | A1* | 12/2008 | Sysko et al. | 705/3 |
| 2010/0070554 | A1* | 3/2010 | Richardson et al. | 709/202 |
| 2010/0076786 | A1* | 3/2010 | Dalton et al. | 705/3 |
| 2010/0189220 | A1* | 7/2010 | Flynn | A61N 5/103 378/65 |
| 2011/0161095 | A1* | 6/2011 | Line et al. | 705/2 |

OTHER PUBLICATIONS

Laitinen, J. O., et al.; The Effect of Three Dimensional Activity Distribution on the Dose Planning of Radioimmunotherapy for Patients With Advanced Intraperitoneal Pseudomyxoma; 1997; Cancer; 80(12)2545-2552.

Sgouros, G.; Dosimetry of Internal Emitters; 2005; J. of Nuclear Medicine; 46(1)18S-27S.

Sgouros, G., et al.; Treatment Planning for Internal Radionuclide Therapy: Three-Dimensional Dosimetry for Nonuniformly Distributed Radionuclides; 1990; J. of Nuclear Medicine; 31(11)1884-1891.

* cited by examiner

DOSE-VOLUME KERNEL GENERATION

CROSS REFERENCE TO RELATED APPLICATIONS

This application claims the benefit of U.S. provisional application Ser. No. 61/047,443 filed Apr. 24, 2008, which is incorporated herein by reference.

The following generally relates to determining a dose-volume kernel for calculating an expected absorbed dose distribution within a patient for planning a radiation therapy treatment and is described in connection with a single photon emission computed tomography (SPECT) scanner. However, the following is also amenable to other medical imaging and non-medical imaging applications such as positron emission tomography (PET) and/or other applications.

Targeted radionuclide therapy (TRT) has been used in the treatment of various diseases such as non-Hodgkins Lymphoma and neuro-endocrine tumors. Generally, TRT involves the administration of a therapeutic isotope (a radionuclide-labeled, cell-specific agent such as an antibody or a peptide) to a patient to kill specific tissue, such as a tumor, corresponding to the specific cell type. The cell-specific agent, or carrier, selectively seeks out such cells, and the radionuclide decays, emitting lethal radiation such as β particles that travel a few millimeters, interacting with and killing or damaging tissue. The success of a treatment generally depends on the amount of radioactivity absorbed or taken up in the tissue of interest and how long it remains localized there. Since it is possible to label the carrier molecule with a diagnostic nuclear isotope (single photon or positron emitter), information about the radioactivity can be obtained in a planning phase by scanning the patient with a SPECT or PET scanner. Some isotopes, such as Iodine-131, are both beta and photon emitters, and that it is possible to administer treatment and see the radiation that delivers the treatment.

Unfortunately, the emitted radiation also interacts with and kills tissue other than the tissue of interest. As a result, it is desirable to determine an expected absorbed dose distribution within the patient during a planning phase (which occurs prior to administering treatment) in order to predict the therapeutic effect to target cells and potential side effects to other cells. Conventionally, the expected absorbed dose distribution has been determined using image data generated by a SPECT or PET scanner, which provides quantitatively accurate activity information. More particularly, for radiation treatment planning purposes a diagnostic isotope such as a SPECT or PET-labeled, cell-specific agent is administered to the patient, and the patient is scanned. One technique for determining the internal dose distribution from nuclear image data is the 3D, voxelized S-value method, including the following processing steps. A three-dimensional dose calculation grid is defined in the resulting image data and, for each voxel in the grid, an estimate of the total number of radioactive decays is determined. This can be achieved by repeating scans over a time period, then integrating the data over the time period, for each voxel, and dividing this value by the amount of injected diagnostic activity to generate a residence-time map, which provides an indication of the total number of decays per injected diagnostic activity in each voxel for the time period.

An expected absorbed dose distribution for each voxel has been determined by convolving the corresponding residence-time map with a three-dimensional array that describes the dose absorbed (deposited) in neighboring voxels due to the amount of radioactivity in a source voxel. This array, referred to as a dose-volume kernel (DVK) herein, is a function of the particular isotope, the tissue material of the voxel, and the voxel size. For isotopes with a short decay particle range on the order of a few millimeters and voxel dimensions of 2 to 10 mm, a DVK consisting of 7×7×7 voxels or smaller is typically sufficient. In order to calculate precise internal dose distributions and to be able to derive meaningful clinical conclusions from them, the used DVK needs to be accurate. Conventionally, a Monte-Carlo technique has been used to pre-calculate suitably accurate DVKs prior to planning. Unfortunately, such an approach can be time intensive (on the order of hours), and each pre-calculated DVK corresponds to a particular voxel size (spatial resolution). As a consequence, a Monte-Carlo technique is not well-suited for on-demand generation of a DVK such as when a DVK is needed during the planning process for computing an expected absorbed dose distribution. Moreover, a DVK for each voxel size of interest for each type of tissue of interest for each isotope of interest would need to be pre-calculated and stored, which may require a high computational effort and large storage space.

Aspects of the present application address the above-referenced matters and others.

According to one aspect, a radiation planning system includes a dose volume kernel determiner and an expected absorbed dose determiner. The dose volume kernel determiner generates a dose volume kernel for each of a plurality of voxels in a dose calculation grid. Each of the dose volume kernels is based on a radial dose distribution and a template function for a desired voxel size. The expected absorbed dose determiner (124) determines an expected absorbed dose distribution for each of the plurality of voxels based on the dose volume kernel.

In another aspect, a method includes generating a template function for a desired voxel size, wherein the template function includes geometric information specific to the voxel size; retrieving a radial dose distribution, wherein the radial dose distribution function represents absorbed dose due to a point source of a therapy isotope as a function of distance from the point source; and generating a dose volume kernel based on the template function and the radial dose distribution.

In another aspect, a method includes prompting a user for a voxel size; notifying the user that there is no dose volume kernel for the voxel size; receiving an input indicative of a type of template function to generate from the user; generating the template function based on the voxel size; obtaining a radial dose distribution; and generating a dose volume kernel as a function of the template function and the radial dose distribution.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
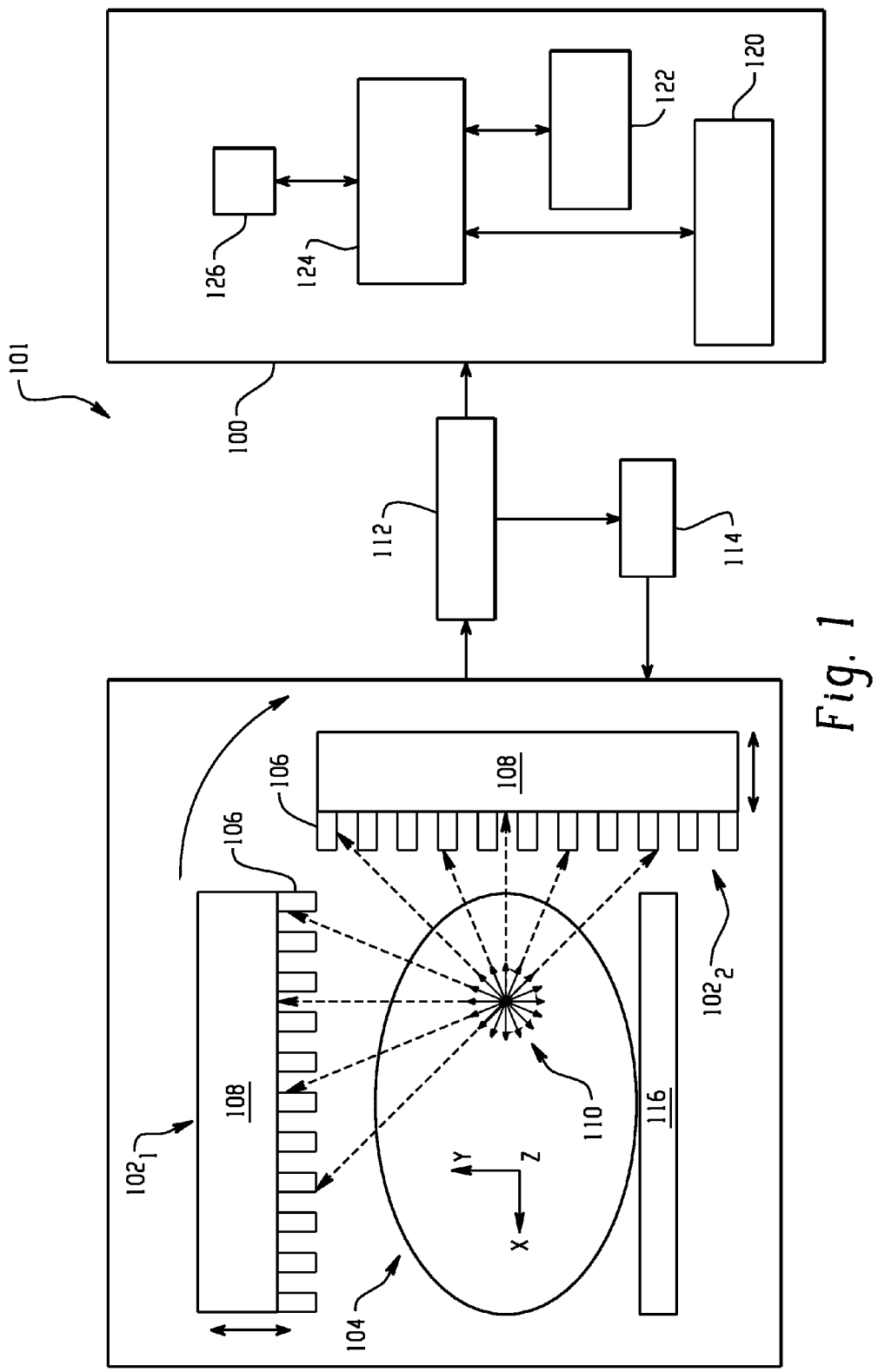
FIG. 1 illustrates a radiation planning system in connection with a medical imaging system.
Figure 2:
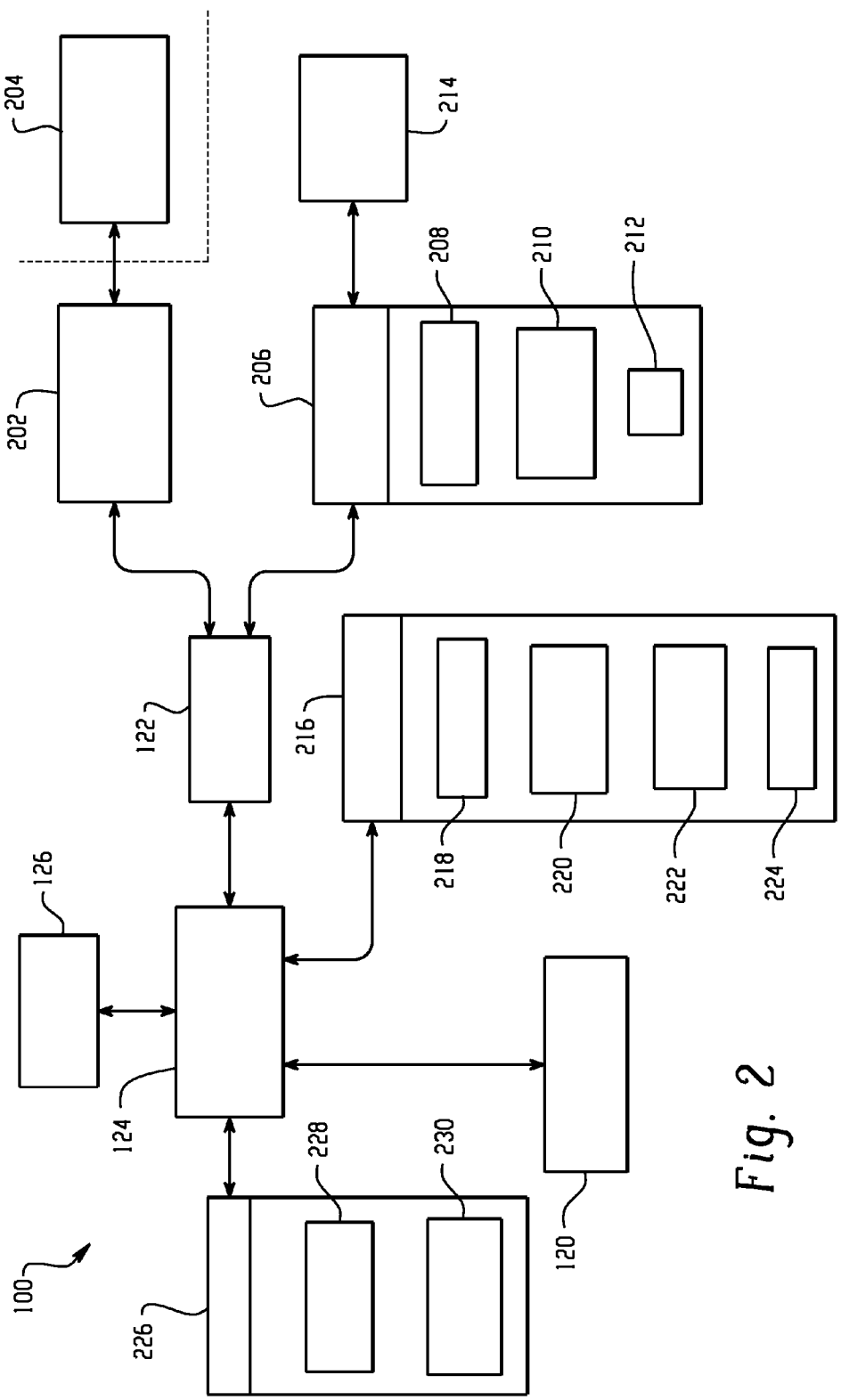
FIG. 2 illustrates an example radiation planning system.

With reference to FIG. 1, a radiation therapy planning (RTP) system 100 can generate an expected absorbed dose distribution for a region of a patient for treatment planning. The RTP 100 system can use image data generated by a single photon emission tomography (SPECT), a positron emission tomography (PET) and/or one or more other emission based scanners that generate data indicative of radioactivity absorbed in a patient for radiation therapy planning and/or other purposes. In addition, the use of further image data from modalities like x-ray CT or MRI is possible for purposes including registration of nuclear medical data, segmentation of organs at risk, etc. For sake of clarity and brevity, the following describes a non-limiting embodiment of the RTP system 100 in connection with a SPECT system 101.

The SPECT system 101 includes at least one gamma radiation sensitive detector, such as gamma cameras $102_1$ and $102_2$. In the illustrated embodiment, the gamma cameras $102_1$ and $102_2$ are disposed relative to each other at an angle of about ninety (90) degrees. In another embodiment, an angle outside of this range is used. The gamma cameras 102 are configured to rotate about a longitudinal or z-axis around an examination region 104 for a plurality of projection angles or views. The gamma cameras 102 may also be configured to translate tangentially with respect to the longitudinal axis. One or more drives are used to rotate and/or translate the gamma cameras 102.

Each of the gamma cameras 102 includes a collimator 106 and a photosensor array 108. The collimator 106 includes a plurality of openings and collimates gamma photons emanating from a radioactive isotope 110 located in the examination region 104. The photosensor array 106 includes a scintillator in optical communication with an array of photomultiplier tubes (PMTs) or semiconductor photodetectors. In another embodiment, the photosensor array 106 includes a direct conversion detector or another light sensitive detector. As the gamma cameras 102 rotate, the scintillators detect gamma photons passing through the collimator openings and produce light in response thereto, and the photosensor arrays generate projection data indicative of the detected gamma photons.

A reconstructor 112 reconstructs the projection data to generate volumetric image data indicative of the distribution of radioisotopes emanating from the examination region 104. A computer serves as an operator console 114 and includes a human readable output device such as a monitor or display and an input device such as a keyboard and mouse. Software resident on the console 114 allows the operator, e.g., via a graphical user interface (GUI), to control operation of the system 101. An object support 116 supports an object, such as a human patient, in the examination region 104.

For radiation therapy planning, an agent labeled with a SPECT diagnostic isotope such $^{111}$In (Indium-111) is administered to the patient, and the patient is scanned with the scanner 101 at a number of different times, relative to the time of the administration of the agent, over a time interval. The resulting image data from each scan is indicative of the amount or concentration of radioactivity in the patient's body at the time of the scan. The image data is provided to the RTP system 100.

An expected absorbed dose determiner 124 of the RTP system 100 determines an expected absorbed dose distribution for each of a plurality of voxels based on a residence-time map for each voxel, which is derived from the image data from the scanner 100, and a dose-volume kernel (DVK) for each voxel, which describes dose deposition around a radioactive source voxel. The total expected absorbed dose for a voxel is determined by summing the expected absorbed dose contributions to the voxel by neighboring source voxels.

A residence-time map generator 120 generates residence-time maps for each voxel. The residence-time map indicates the total number of decays in the corresponding voxel per injected amount of activity over the scan time interval. In one instance, the residence-time map generator 120 derives the residence-time map for a voxel by integrating the activity in the voxel over the time interval. A dose-volume kernel (DVK) determiner 122 determines the DVK, which, as noted above, is a function of voxel size, the isotope of interest, and the tissue of interest. The DVK can be pre-calculated or calculated on-demand during planning as described in greater detail below.

A user interface (UI) 126 allows a user and the RTP system 100 to interact with each other. Such interaction may include exchanging information used to facilitate determining the expected absorbed dose map.

In one instance, generating the DVK on-demand during planning as described herein reduces DVK computation time and/or increases DVK flexibility, while providing the accuracy achieved by generating a DVK through a Monte-Carlo technique. In addition, a DVK can be calculated at any desired voxel size on-the-fly from a pre-calculated or on-demand calculated template function with the speed needed for interactive dose calculation.

A more detailed description of an exemplary embodiment of the RTP system 100 is provided next in connection with FIGS. 2-5. Initially referring to FIG. 2, the DVK determiner 122 determines a DVK for an expected dose distribution calculation based on a radial dose distribution and a suitable template function. In once instance, the DVK determiner 122 determines the DVK for a particular voxel by sampling the radial dose distribution to a desired voxel size (resolution) using a template function. For example, the DVK value for a voxel (i,j,k) can be calculated using the following integral:

$$DVK(i, j, k) = \frac{1}{m_{voxel}} \int_0^\infty D(r) \cdot h_{i,j,k}(r) dr,$$

wherein D(r) is the radial dose distribution as a function of the distance r in units of Joule/(Decay*mm) and $h_{i,j,k}(r)$ is the template function as a function of the distance r (unitless). The DVK is in units of Grays/Decay. By multiplying the template function with the stored radial dose distribution and integrating the result, an accurate DVK value can be quickly calculated on-the-fly.

Figure 3:
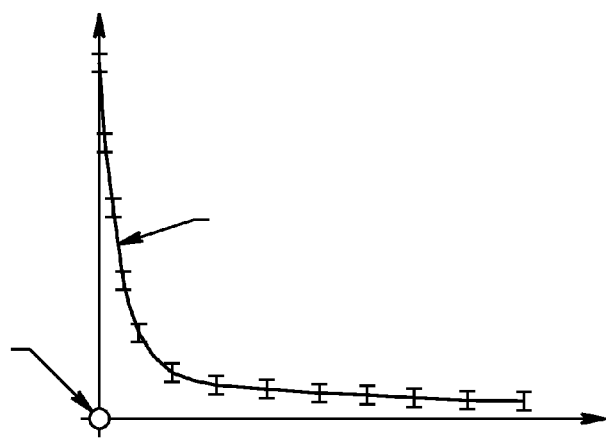
FIG. 3 illustrate an example radial dose distribution function.
Figure 4:
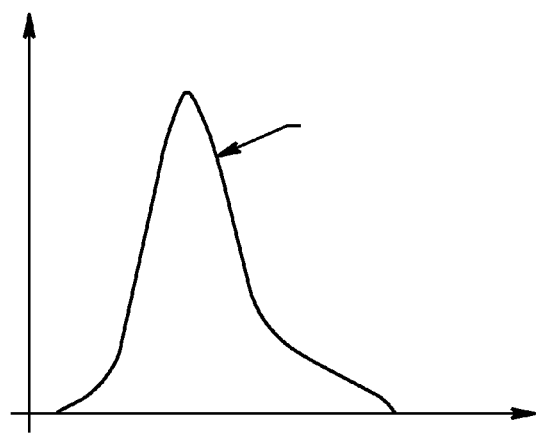
FIG. 4 illustrate an example template function.

Briefly turning to FIG. 3, an example radial dose distribution is shown. The y-axis represents absorbed dose, the x-axis represents the distance from the point source, and the distribution represents the absorbed dose as a function of the distance from the point source. Turning to FIG. 4, an example template function is shown. The y-axis represents a relative frequency of lengths of lines that connect a source and a target voxel, the x-axis represents the distance between the locations in the source and the target voxels (with the minimum and maximum distance indicated as $l_{min}$, $l_{max}$), and the distribution represents a histogram as a function of the distances between the source and target voxels. This histogram contains the geometry information specific to a voxel grid of given dimensions and can be referred to as a geometrical template function.

Returning to FIG. 2, the radial dose distribution is stored in a radial dose distribution bank 202, which can store one or more radial dose distributions. A radial dose distribution determiner 204, which may be or may not be part of the RTP system 100, determines the radial dose distribution. In one instance, a radial dose distribution is determined using a Monte-Carlo technique. This can be done prior to planning, in which the radial dose distribution is stored in the radial dose distribution bank 202 and/or elsewhere for subsequent use, or during planning. In this example, the radial dose distribution is a distribution for a point-source of the therapeutic isotope. Such a distribution may represent deposited dose caused by a point source of the therapy isotope in tissue equivalent material. When using a point source, a one-dimensional radial dose distribution can be generated due to the spherical symmetry of the underlying geometry (point source and tissue). The example radial dose distribution in FIG. 3 represents a one-dimensional radial dose distribution computed using a Monte-Carlo technique. Other techniques may alternatively be used to determine the radial dose distribution.

The template function is stored in a template function bank 206, which can store one or more template functions. In the illustrated example, the template function bank 206 stores at least one of a cubic grid template function 208, an arbitrary (super) grid template function 210, or a three-dimensional (3D) template function 212. A template function generator 214 and/or another component generates such template functions. The template function generator 214 may also generate a template function on-the-fly, for example, using a stochastic approach, as described in greater detail below.

The cubic grid template function 208 can be used when the desired voxel size is cubic in that the length of each side of the voxel is equal. In this case, a universal template function, sufficient for a reference voxel size, can be generated and used for all cubic voxel sizes. For cubic voxels of size other than the reference voxel size, the cubic grid template function is scaled to the appropriate size. That is, the cubic grid template function only needs to be scaled up or down to the true dimension of the voxels. As such, a single cubic grid template function 208 can be pre-calculated and stored for subsequent use.

By way of example, if the cubic grid template function (h'(r)) represents a unit length cubic voxel for the minimum voxel size, then the cubic grid template function (h'(r)) is used when the voxel size is the required voxel size, and the cubic grid template function (h'(r)) is scaled to generate a suitably scaled cubic grid template function (h(r)) when the voxel size is the greater than the reference voxel size. In one instance, the suitably scaled cubic grid template function is generated as follows: h(r)=h'(r/a), wherein a is a side length other than unity. Other coordinate transformations may alternatively be used. It is to be appreciated that a cubic voxels may be 1×1×1 mm or larger such as 10×10×10 mm. Smaller and larger sizes may also be used.

The arbitrary (super) grid template function 210 can be used with both cubic and non-cubic voxels. In one instance, the arbitrary grid template function 210 includes a plurality of fine resolution cubic grid template functions, each with dimensions that are smaller than the minimum voxel size. In one embodiment, the larger grid has a side length such that an integer number of smaller grid voxels fits into each of the larger voxels. For instance, a suitable voxel may include 3×6×4 smaller grid voxels. As such, a suitable template function for a particular voxel size (cubic and non-cubic) is generated by summing the template functions for all contributing smaller voxels.

For example, the arbitrary grid template function 210 may include a set of cubic grid functions for a smaller cube with a side length of about 0.01 or 0.05 mm for a minimum non-cubic larger voxel size of A×B×C mm, wherein at least one of A, B or C is greater than 0.01 or 0.05 mm. Each larger voxel can then be represented as a set union of all smaller cubic voxels that are located inside the larger voxel. By way of example, if the arbitrary grid template function ($g_{i,j,k}(r)$) of the smaller cubes is pre-calculated, then the template function (h(r)) for the selected larger voxel size can be calculated by superposition by adding the relevant g-functions as follows:

$$h_{a,b,c}(r) = \sum_{l,m,n}\sum_{o,p,q} g_{|o-l|,|p-m|,|q-n|}(r),$$

with (i,j,k) such that the starting g-functions are out of the source voxel $V_{0,0,0}$ of the larger grid and (o,p,q) such that the end g-function are out of the target voxel $V_{a,b,c}$ of the larger grid.

Similarly, the 3D grid template function 212 can be used with both cubic and non-cubic voxels. For this template function, the distance histograms (probability density) in each dimension separately have a well-known shape, which is a triangular function. As such, only three points need to be stored for each triangular function, which may save space relative to other template function types. One approach for calculating such a template function is to subdivide the distance space into fine divisions, calculate for each set of vector components (x, y, z) which form a distance vector the joint probability density for these components (the product of the one-dimensional probability densities), and then add them to the respective distance bin for that distance vector. By way of example, let the template functions in each single coordinate direction be $s_a(x)$, $t_b(y)$, $u_c(z)$. Then, the full 3D template function can be calculated as $$h_{a,b,c}(r) = \int\int_K\int s_a(x) \cdot t_b(y) \cdot u_c(z) dx dy dz,$$

wherein K is the integration range. As such, the 3D template function 212 is based on all combinations of x, y, z that fulfil the relation $r^2=x^2+y^2+z^2$.

As briefly noted above, the template function generator 214 additionally or alternatively generates template functions on-the-fly during planning. For example, the template function generator 214 can generate a template function using stochastic sampling. For instance, a template function for a target voxel, with respect to the source voxel, can be computed by determining a distance between randomly placed start and end points respectively within a source and target voxel, for a plurality of start and end points. In this example, the distance is a Euclidian distance. A respective bin in a distance histogram is then incremented.

A suitable template function, in the form of a distance histogram, can be generated by repeating this for a large number of start and end point samples. By way of example, let p be an arbitrary position in a source voxel $V_{0,0,0}$ and q be an arbitrary position within a target voxel $V_{a,b,c}$, chosen by a stochastic experiment (i.e. random number generator).

Figure 5:
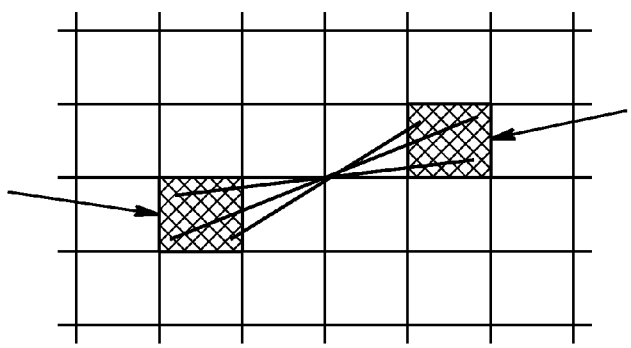
FIG. 5 illustrate an example technique for determining a template function using a stochastic approach.

A histogram can be generated by incrementing each bin $h_{a,b,c}(r_i)$ when, for a pair of p, q, the distance |p−q| is between $r_i$ and $r_{i+1}$. This can be repeated for a large number of points and normalized by dividing the histogram by the number of points. The noise level can be reduced by using a sufficient number of start and end points. FIG. 5 graphically illustrates a plurality of distances between start and end points in source and target voxels.

Returning to FIG. 2, a parameter bank 216 stores parameters used to facilitate computing the expected absorbed dose. As shown, suitable parameters include, but are not limited to, at least one of a voxel size 218, a number of start and end points 220, an error threshold 222, or an auto flag 224. As noted above, the voxel size 218 is used when determining and/or generating a DVK as the DVK is a function of the voxel size. The number of start and end points 220 is used when stochastically determining the template function. The error threshold 222 may be used to determine a suitable number of start and end points to achieve a desired level accuracy, or limit the inaccuracy. The auto flag 224 is used to determine whether a DVK is automatically generated when a suitable DVK is not available or whether the user should be prompted that a suitable DVK is not available. When the flag 224 is set to indicate automatic generation, a DVK can be generated behind the scenes without user interaction. Otherwise, the RTP system 100 interacts with the user for input when generating a DVK.

A DVK bank 226 is used to store DVKs. DVKs stored in the DVK bank 226 include pre-calculated DVKs such as those calculated prior to planning using a Monte-Carlo or other technique, and DVKs that have been calculated on-demand such as one or more of those generated by the DVK determiner 122. In one embodiment, the DVK bank 226 is omitted.

The user interface 126, which may be a graphical and/or a command line user interface, receives and/or presents information to a user. For example, a user may provide information such as the voxel size 218, the treatment isotope (e.g., Y-90), the tissue type of interest in the treatment, an indication of a particular template function to use for computing a DVK for the voxel size 218, one or more other parameters used to compute the DVK such as the number of start and end points 220, the error threshold 222, the flag 224, and/or other information. This information may be provided by the user in response to a notification from the RTP system 118 that is presented to the user, while the user navigates through a RTP application, upon execution of a script, etc. The information presented to the user may include a request for a desired voxel size, an indication that a DVK for the desired voxel size is not currently available, a prompt for an input indicative of whether a DVK should be computed, a list of available template function to choose from, an expected time to compute a DVK, and/or other information.

Figure 6:
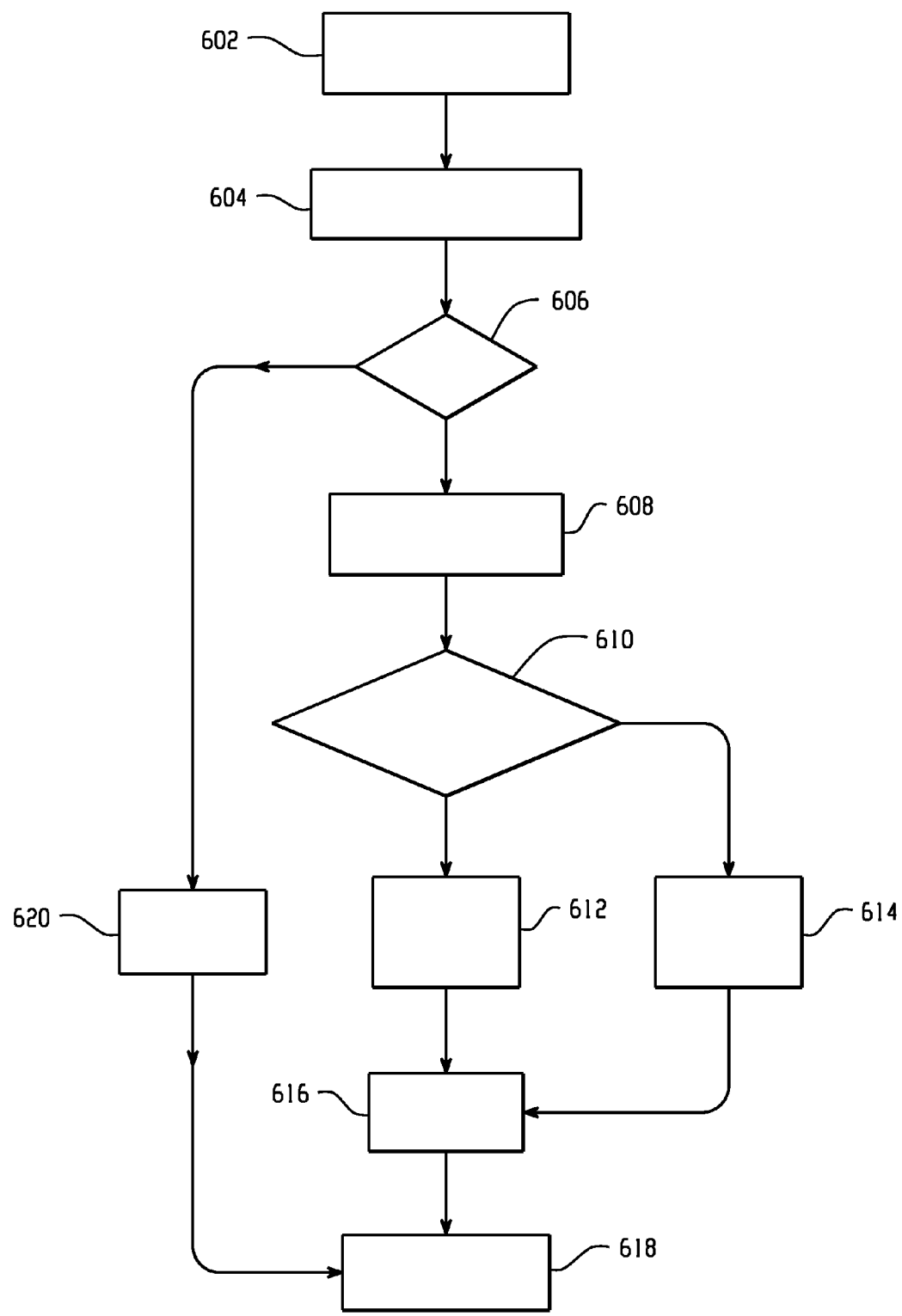
FIG. 6 illustrates a method.

Operation will now be described with reference to FIG. 6.

At 602, the voxel size for an expected absorbed dose is obtained. As noted above, this information may be obtained from a user via a user interface 126 and/or the parameter bank 216.

At 604, a residence-time map is determined. As discussed herein, the residence-time map is generated based on image data from the SPECT scanner 100 and/or another emission based scanner such as a PET scanner or the like.

At 606, it is determined whether a DVK of suitable resolution (voxel size) is available.

If not, then at 608 a radial dose function is retrieved.

Then, at 610, it is determined whether a stored template function or a template function generated on-the-fly is to be used.

If a stored template function is to be used, then at 612 a suitable stored template function is obtained. If more than one template function is stored, the particular template function obtained may be indicated by a user, a user defined priority, and/or automatically, for example, based on information such as the voxel dimensions and/or other information.

If a template function is to be generated on-the-fly, then at 614 the template function is generated for the voxel size.

At 616, the DVK is generated on-the-fly based on the radial dose distribution and the template function.

At 618, the expected absorbed dose is generated based on the residence-time map and the DVK.

If at 608, it is determined the suitable DVK is available, then at 620 the DVK is obtained, and at 618 the expected absorbed dose is generated based on the residence-time map and the DVK. As noted above, such a DVK may be pre-calculated or previously calculated on-the-fly.

The above may be implemented by way of computer readable instructions, which when executed by a computer processor(s), cause the processor(s) to carry out the described techniques. In such a case, the instructions are stored in a computer readable storage medium associated with or otherwise accessible to the relevant computer. The described techniques need not be performed concurrently with the data acquisition.

Although the RTP system 100 is shown as separate from the scanner 101, in another embodiment the RTP system 100 is part of the scanner 101, for example, software executed on the console 114. In another embodiment, the RTP system 100 is remotely located from the scanner 101.

The invention has been described with reference to various embodiments. Modifications and alterations may occur to others upon reading the detailed description. It is intended that the invention be constructed as including all such modifications and alterations insofar as they come within the scope of the appended claims or the equivalents thereof.

The invention is claimed to be:
1. A radiation treatment planning system comprising:
a dose volume kernel determiner that determines a dose volume kernel of a targeted radionuclide therapy for each of a plurality of voxels in a dose calculation grid in image data generated by one of a SPECT scanner or a PET scanner, and the dose volume kernel includes a multi-dimensional array that describes a dose absorbed in neighboring voxels due to an amount of radioactivity of a radionuclide in a source voxel;
wherein the dose volume kernel determiner determines the dose volume kernel for a voxel of the plurality of voxels by sampling a single pre-calculated and stored radial dose distribution, which is pre-calculated around a point source and represents an absorbed dose due to the point source of a therapy isotope as a function of distance from the point source to a predetermined voxel size using a template function for the predetermined voxel size corresponding to a size of the voxel;
an expected absorbed dose determiner that determines an expected absorbed dose distribution for each of the plurality of voxels based on the dose volume kernel; and
a user interface that displays an expected absorbed dose map with a total expected absorbed dose determined for each voxel using the determined expected absorbed dose distribution.

2. The system of claim 1, wherein the template function includes geometric information specific to the voxel size and is selected based on the voxel size.

3. The system of claim 1, wherein the dose volume kernel determiner determines the dose volume kernel by determining a product of the pre-calculated radial dose distribution and the template function and integrating the product.

4. The system of claim 1, wherein the template function is a scalable cubic template function of sufficient size for a reference size cubic voxel having equal length sides, wherein the template function is scaled to the voxel size.

5. The system of claim 1, wherein the template function includes a summation of cubic voxel template functions for a cubic voxel that is smaller than a minimum voxel size, wherein the cubic voxel template functions are summed to generate a single template function for a larger voxel of at least the minimum voxel size.

6. The system of claim 5, wherein the larger voxel is not cubic.

7. The system of claim 1, wherein the template function is a summation of three one-dimensional template functions.

8. The system of claim 7, wherein a shape of each of the three one-dimensional template functions is a triangular function.

9. The system of claim 1, wherein the template function is the joint probability density function of three single dimension probability density functions.

10. The system of claim 1, further including a template function determiner that generates the template function based on stochastic sampling.

11. The system of claim 10, wherein the template function represents a normalized frequency of distances between randomly placed start and end points respectively in a source and a target voxel.

12. The system of claim 1, wherein the template function is generated during planning.

13. The system of claim 1, wherein the dose volume kernel determiner determines the dose volume kernel on-demand in that the dose volume kernel is not pre-calculated, but calculated when needed to determine the expected absorbed dose distribution.

14. A method, comprising:
generating a template function for a particular voxel size, wherein the template function includes geometric information specific to the voxel size;
retrieving, by a processor, a pre-calculated radial dose distribution, wherein the pre-calculated radial dose distribution function represents absorbed dose due to a point source of a therapy isotope as a function of distance from the point source;
generating a dose volume kernel of a targeted radionuclide therapy for the voxel size based on the template function and the radial dose distribution by sampling the pre-calculated radial dose distribution to the voxel size by calculating a product of the pre-calculated radial dose distribution and the template function and integrating the product, and the dose volume kernel includes a multi-dimensional array that describes a dose absorbed in neighboring voxels due to an amount of radioactivity of a radionuclide in a source voxel in a dose calculation grid in image data generated by one of a SPECT scanner or a PET scanner;
displaying an expected absorbed dose map with a total expected absorbed dose determined for each voxel using the generated dose volume kernel.

15. The method of claim 14, further including generating an expected absorbed dose distribution for the therapy isotope based on the dose volume kernel and a residence-time map.

16. The method of claim 14, further including generating the dose volume kernel by sampling the radial dose distribution to a voxel grid for the voxel size using the template function.

17. The method of claim 14, further including generating the template function during radiation therapy planning.

18. The method of claim 14, further including pre-calculating and storing the template function for subsequent radiation therapy planning.

19. The method of claim 14, further including generating the dose volume kernel during radiation therapy planning.

20. The method of claim 14, further including generating the dose volume kernel on-demand, when needed for generating an expected absorbed dose distribution.

21. The method of claim 14, wherein the template function is a cubic template function of sufficient size for a reference size cubic voxel, and further including scaling the template function to the voxel size.

22. The method of claim 15, further including summing a plurality of smaller cubic voxel template functions to generate a single template function for a larger voxel having at least one side with a length greater than the side lengths of the individual cubic voxels.

23. The method of claim 15, further including summing three one-dimensional template functions to generate a three-dimensional template function.

24. The method of claim 15, further including generating the template function through stochastic sampling, wherein the template function is a histogram of distances between randomly placed start and end points respectively in a source and a target voxel.

25. A method, comprising:
prompting a user for a voxel size;
notifying the user when there is no dose volume kernel of a targeted radionuclide therapy for the voxel size available from a system;
receiving an input indicative of a type of template function to generate from the user;
generating the template function based on the voxel size;
obtaining a pre-calculated radial dose distribution, which is pre-calculated around a point source and represents an absorbed dose due to the point source of a therapy isotope as a function of distance from the point source; and
generating, by a processor, a dose volume kernel for the voxel size by calculating a product of the pre-calculated radial dose distribution and the template function and integrating the product, and the dose volume kernel includes a multi-dimensional array that describes a dose absorbed in neighboring voxels due to an amount of radioactivity of a radionuclide in a source voxel in a dose calculation grid in image data generated by one of a SPECT scanner or a PET scanner;
displaying an expected absorbed dose map with a total expected absorbed dose determined for each voxel using the generated dose volume kernel.

26. The method of claim 25, further including generating an expected absorbed dose for a therapy isotope based on the generated dose volume kernel.

27. The method of claim 25, further including prompting the user for a number of start and end points used to generate the template function through stochastic sampling.

28. The method of claim 25, further including prompting the user for a threshold error value used to determine a suitable number of start and end points used to generate the template function through stochastic sampling.

* * * * *